United States Patent [19]

Karacan et al.

[11] 4,103,678
[45] Aug. 1, 1978

[54] NOCTURNAL PENILE TUMESCENSE MONITOR

[75] Inventors: Ismet Karacan, Houston, Tex.; Larry G. Paulson; Gerald W. Timm, both of Minneapolis, Minn.

[73] Assignee: American Medical Systems, Inc., Minneapolis, Minn.

[21] Appl. No.: 789,713

[22] Filed: Apr. 21, 1977

[51] Int. Cl.² ........................ A61B 5/00; G01D 15/10
[52] U.S. Cl. ................... 128/2.05 V; 128/2 S; 346/33 ME; 346/34; 346/62;76 R; 346/76 R
[58] Field of Search ................ 128/2 R, 2 S, 2.05 Q, 128/2.05 V, 2.06 G; 346/33 ME, 34, 62, 76 R; 219/216

[56] References Cited

U.S. PATENT DOCUMENTS

| | | | |
|---|---|---|---|
| 3,200,404 | 8/1965 | Ott | 346/34 |
| 3,467,810 | 9/1969 | Cady, Jr. | 219/216 |
| 3,648,689 | 3/1972 | Dominy | 346/34 X |
| 3,754,279 | 8/1973 | Valenti et al. | 346/76 R |
| 3,840,878 | 10/1974 | Houston et al. | 219/216 |
| 3,893,453 | 7/1975 | Goldberg et al. | 128/2.06 G |
| 3,894,533 | 7/1975 | Cannon | 128/2.05 Q X |
| 3,908,641 | 9/1975 | Judson et al. | 346/33 ME X |
| 3,922,686 | 11/1975 | France et al. | 128/2.06 G X |

OTHER PUBLICATIONS

Ray, C. D., "Medical Engineering", Yrbk Pulbishing, Chic., 1974, p. 443.
Hokanson, et al., "Electrically Calibrated Plethysmograph for Direct Measurement of Limb Blood Flow", IEEE Trans. on Biomed. Engr., vol. BME-22, No. 1, Jan. 1975, pp. 25-29.

Primary Examiner—Robert W. Michell
Assistant Examiner—Frank Jaworski
Attorney, Agent, or Firm—Williamson, Bains, Moore & Hansen

[57] ABSTRACT

Apparatus for generating and recording signals from two separate sensors on a patient adapted to provide an indication of the condition of an anatomical member to be monitored.

A control cabinet having an integral strip chart recorder is provided with plug in inputs for two externally connected strain gauges. Each strain gauge makes up one leg of a bridge circuit. The bridge outputs are amplified and multiplexed into a single channel strip chart recorder having a single, heated stylus which records two separate traces based on the signals received from the two sensors.

Heat to the recordinng pen or stylus is turned off during switching excursions of the pen between the two traces so as to eliminate shading and marking which would otherwise occur on the recording chart between the traces at slow chart speeds. In the nocturnal penile tumescence monitoring application for which the apparaus is primarily intended, two mercury strain gauges in the form of elastomer rings are positioned at the base and tip of the penis. Minute variations in penile size occurring during the Rapid Eye Movement stages of sleep are sensed by the strain gauges, amplified, through bridge circuits and recorded in two separate traces.

19 Claims, 7 Drawing Figures

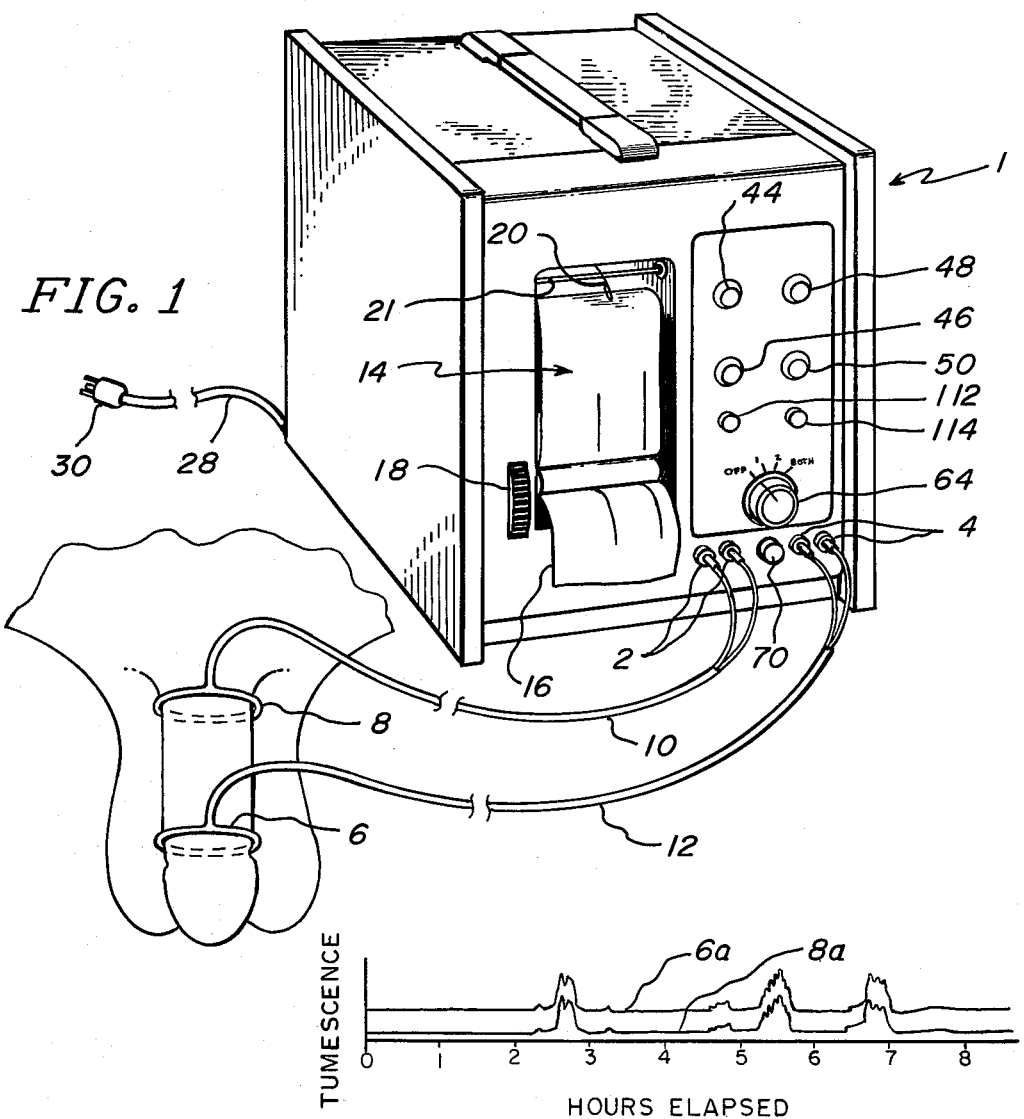
FIG. 1
FIG. 2
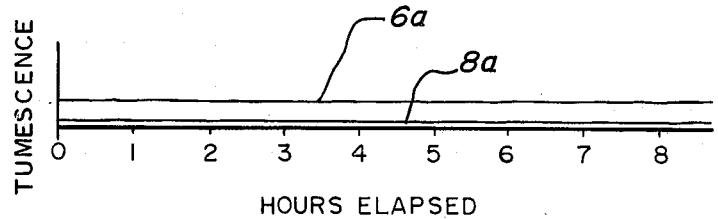
FIG. 3

NOCTURNAL PENILE TUMESCENSE MONITOR

BACKGROUND OF THE INVENTION

Recognition that nocturnal penile tumescence monitoring can be of assistance in diagnosing male erectile impotence has led to the development of various types of devices and techniques for conducting such monitoring. In an article entitled "A Simple and Inexpensive Transducer for Quantitative Measurements of Penile Erection During Sleep", *Behavior Research Methods and Instrumentation*, Volume 1, Pages 251-252, 1969, Ismet Karacan describes a mercury strain gauge transducer for measuring penile erection, the transducer being in the form of an elastomer ring. A number of devices and procedures for monitoring penile tumescence during sleep are noted and referenced in an article entitled "Sleep-Related Penile Tumescence as a Function of Age", *American Journal Psychiatry*, Volume 132, page 9, September 1975. Strip chart recording instruments capable of recording two traces from input signals with a single, heated pen are also known. Such an instrument is manufactured by Astro-Med, Division of Atlan-Tol Industries, Inc., West Warwick, Rhode Island.

We have discovered that a particularly clear and objective view of the part that organic causes play in male erectile impotence can be achieved by utilizing two strain gauges attached to the base and tip of the penis. Effective monitoring and recording of tumescence variations sensed by the two strain gauges is accomplished by a specially designed strip chart recorder of the single stylus, multiplexing type.

BRIEF SUMMARY OF THE INVENTION

The monitoring and recording instrument of this invention has been developed with a view towards providing an accurate means of obtaining and recording diagnostic data from two separate locations on a patient over extended recording intervals with minimum disturbance of the patient and with the generation of manageable amount of recording chart paper.

These basic objectives have been realized by utilizing a strip chart recorder capable of recording two traces from two separate input signals with a single pen or stylus. The heat sensitive recording paper is advanced past the heated pen at a predetermined slow speed which provides a meaningful trace record of two input signals on a minimum amount of recorded paper over relatively long recording periods of eight hours or more.

The instrument has plug in connections for receiving signals from two externally located sensing devices. With the primary anticipated application being the measurement of changes in size of anatomical members, the sensing devices advantageously take the form of elastomer strain gauge rings, each of which form one leg of separate, signal generating bridge circuits. The strain gauges change impedance as they expand and contract with variations in the circumference of an anatomical member on which they are mounted. As a result, the separate bridge circuits generate responsive signals which are amplified and transmitted to a drive motor for the recording pen through an analog switch. A controller, preferably in the form of a clock oscillator, emits control signals which are transmitted to trip the analog switch to cycle between the two diagnostic signals at a predetermined frequency.

As a particularly advantageous feature, controls are provided which operate to cyclically de-energize the pen heater during switching excursions of the recording pen between the two traces. This substantially eliminates pen marking and shading between the traces at relatively slow chart speeds.

The cycling of the pen heater is effectively accomplished by a signal relaying device, such as an SCR which transmits energizing signals from the aforesaid clock oscillator to the pen heater at a predetermined frequency with respect to the cycling frequency of the analog switch, such that the pen heater is de-energized during switching movement of the pen between traces on the recording paper. A frequency divider between the clock oscillator and the analog switch ensures that the tripping frequency of the analog switch is so regulated with respect to the rate of pen heater cycling that the pen heater will be de-energized and cooled down during the last half of each recording interval. This further lessens the possibility of pen marking between traces.

Another beneficial aspect of the instrument of this invention resides in the provision of warning indicators, such as, lights, which are automatically activated if the strain gauge sensing devices are broken or improperly connected. This ensures that false signals will readily be detected thereby avoiding improper diagnosis.

The instrument and apparatus disclosed herein is particularly adapted for monitoring nocturnal penile tumescence. It has been found that a particularly effective diagnosis can be made for purposes of distinguishing between organic and psychogenic causes of male erectile impotence by utilizing two tumescence sensitive strain gauges at longitudinally spaced locations on a subject's penis. The strain gauges are connected through signal generating bridge circuits with an analog switch of a strip chart recorder of the above described construction and operation.

These and other objects and advantages of this invention will become readily apparent as the following description is read in conjunction with the accompanying drawings wherein like reference numerals have been used to designate like elements throughout the several views.

BRIEF DESCRIPTION OF THE DRAWINGS

FIG. 1 is a perspective view of the recording instrument of this invention showing the manner of application for nocturnal penile tumescence monitoring;

FIGS. 2 and 3 are typical, condensed tracings of nocturnal penile tumescence activity;

DESCRIPTION OF THE PREFERRED EMBODIMENT

Figure 4:
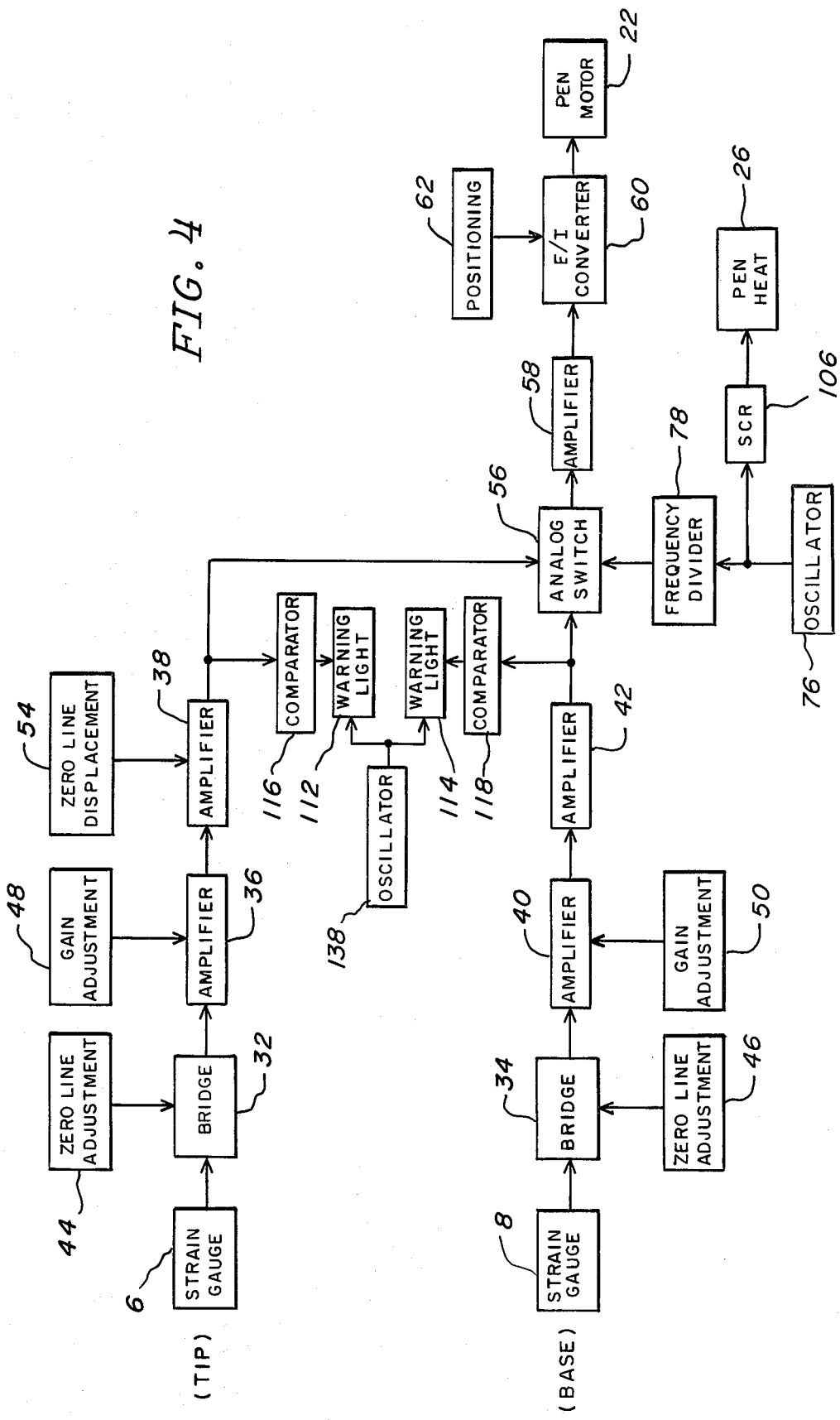
FIG. 4 is a block diagram of the monitoring and recording apparatus of this invention.
Figure 5:
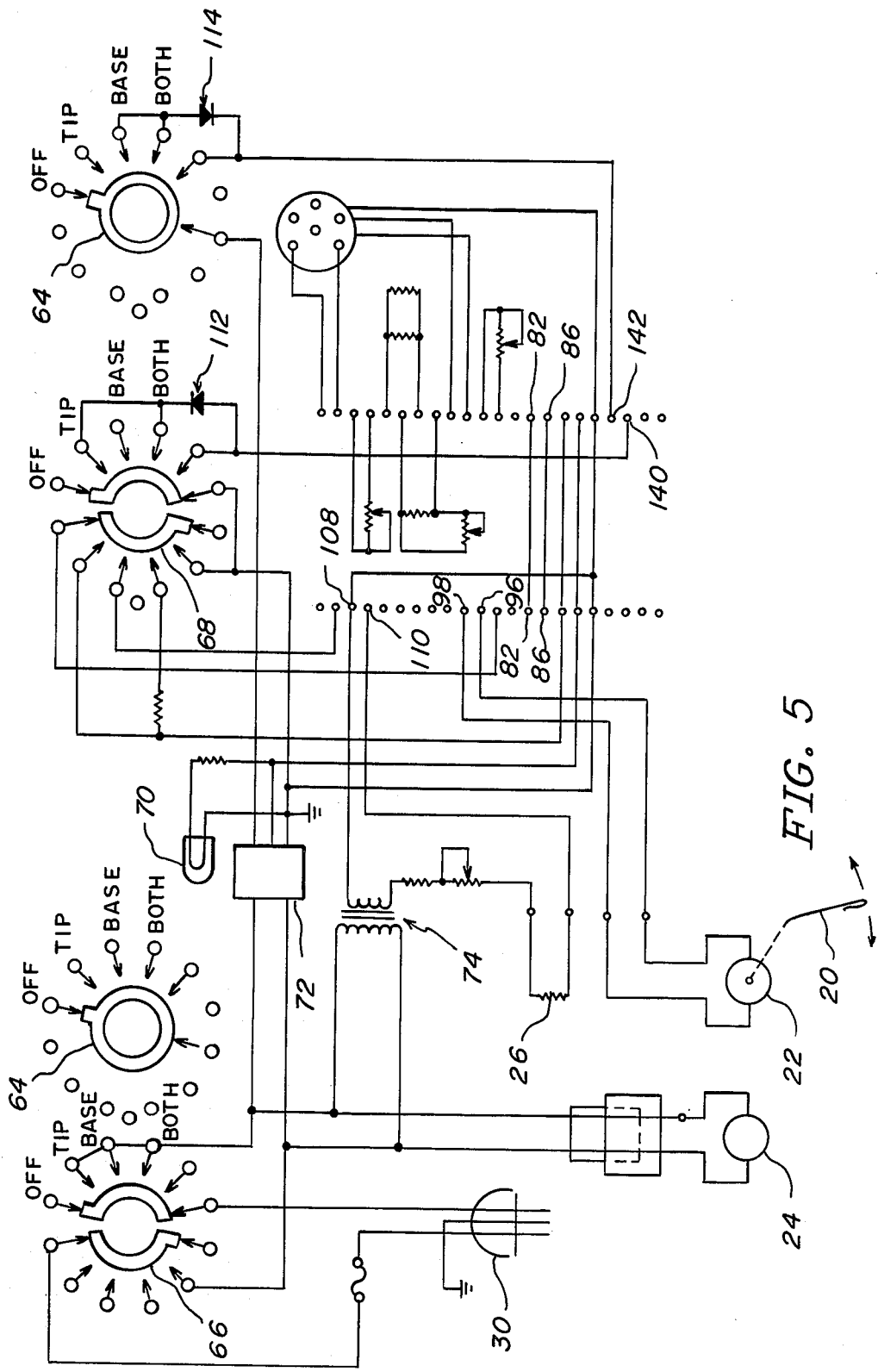
FIG. 5 is a schematic, circuit diagram for the recording and monitoring unit shown in FIG. 1.

Referring now to the drawings, there is shown in FIG. 1, and schematically in FIG. 4, a preferred embodiment of the recording instrument of this invention, and its component parts. This instrument consists of a control cabinet 1 having an integral strip chart recorder and input connections 2 and 4 for a plug in set of two externally connected sensing devices. Preferably, for reasons clarified hereinafter, the sensing devices comprise strain gauges 6 and 8. The cable assemblies 10 and 12 for each strain gauge each include a pair of lead wires connected as shown to plug in connections 2 and 4 on the instrument panel. The strip chart recorder generally indicated by reference numeral 14 utilizes heat sensitive recording paper 16. A manual advance knob 18 is provided for loading and positioning recording paper. The single recording pen or stylus 20 is positioned in trace producing relation to recording paper 16 in a standard manner and is actuated to produce two separate traces by a drive motor 22 in response to signals from the two strain gauges or sensing devices 6 and 8. FIG. 5 illustrates schematically the driving connection between motor 22 and recording pen 20. Pen 20 moves back and forth between the two traces being recorded on a support bar 21 as shown in FIG. 1.

Figure 6:
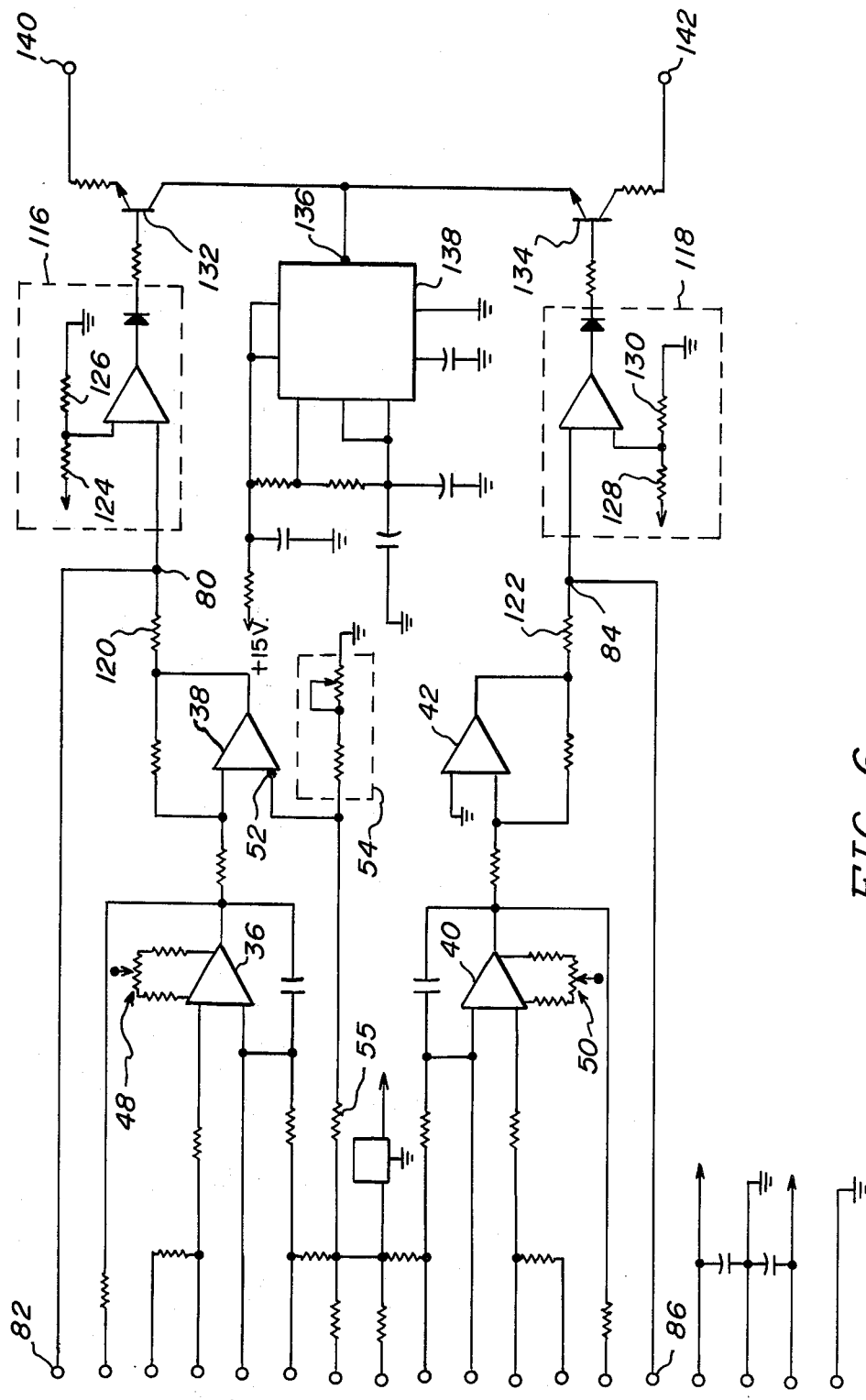
FIG. 6 is a diagram of the output circuits from the Wheatstone bridges to which the strain gauge sensing devices are connected.

Chart paper 16 is guided around a support rod and drive roller in a well known manner, power being supplied to the drive roller for advancing the chart paper at a predetermined speed by a motor 24 shown in FIG. 5. Heat is supplied to the tip of recording pen 20 by a heating element 26 indicated schematically in FIG. 4 and shown in the circuit diagram of FIG. 5. 115 volt, 60 cycle power is supplied to the wired chassis or main frame of the instrument 1 by a power cord 28 and plug 30. The instrument circuitry consists of the wired chassis and two plug in circuit boards having the circuits illustrated in FIGS. 6 and 7. The main frame circuitry as shown in FIG. 5 incorporates the pen drive motor 22, chart motor 24, pen heating element 26, and associated controls and indicators together with connectors for the circuit boards and sensors as hereinafter set forth. The two plug in circuit boards as shown in FIGS. 6 and 7 contain substantially all of the associated control electronics.

Strain gauge sensing devices 6 and 8 are preferably constructed as ring shaped members from elastomer material. To this end silicone elastomer loops as shown in FIG. 1 are filled with mercury to form the strain gauges. Each strain gauge constitutes one leg of a standard Wheatstone bridge circuit. Thus, as the strain gauges expand and contract with variations in the circumference of the anatomical member on which they are mounted, they change impedance. This produces a varying output signal from the brige circuits in which the strain gauges are connected. In FIG. 4 the two separate bridge circuits 32 and 34 are illustrated schematically. These bridge circuits are Wheatstone bridge circuits of well known design and are therefore not shown in detail. The output signals from the two bridge circuits are amplified and multiplexed into the single channel strip chart recorder 14. The first and second stage amplifiers 36 and 38 for strain gauge 6 are shown in FIGS. 4 and 6. The same figures illustrate the first and second stage amplifiers 40 and 42 for strain gauge 8 and its bridge circuit 34. Each bridge circuit has a zero line adjustment 44, 46, respectively, the control knobs for which are shown on the front panel of control cabinet 1 in FIG. 1. This adjustment compensates for differences between individual strain gauges. Similarly, the gain of each of the initial amplification stages is adjustable by variable resistance controllers 48, 50, respectively as shown in FIGS. 4 and 6. The corresponding control knobs for these adjustments on the instrument panel are designated by the same reference numerals in FIG. 1. The input circuits from the two bridges are otherwise identical except that the second amplifier stage 38 for bridge circuit 32 and strain gauge sensor 6 adds a preset increment to the signal that shows up as a positive displacement between the two traces recorded by pen 20 on the strip chart recorder. The bias signal for displacing the traces of the two input signals from each other on recording paper 16 is introduced to terminal 52 of second stage amplifier 38 by means of a voltage divider consisting of the resistance elements shown at 54 and 55 in FIG. 6. The foregoing adjustments are utilized as described below in calibrating the instrument at the time of use.

Figure 7:
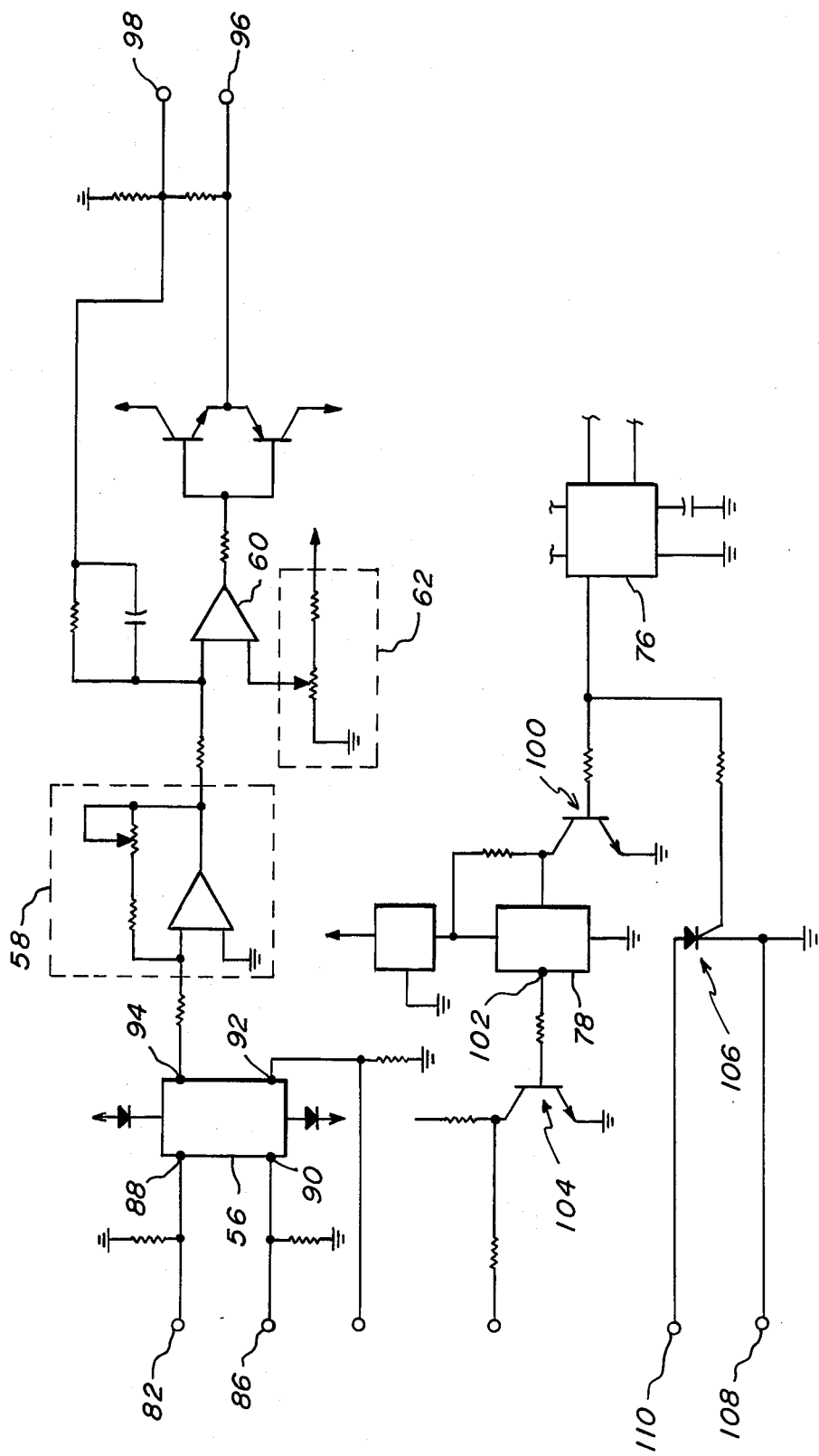
FIG. 7 is a circuit diagram of the control arrangement utilized for switching a recording pen between traces and cycling the pen heater.

Multiplexing of the separate diagnostic signals from the two strain gauges and their respective bridge circuits 32, 34 to actuate pen drive motor 22 is accomplished by switch means which preferably takes the form of an analog switch 56 shown in FIGS. 4 and 7. The output of analog switch 56 drives the pen motor 22 by way of a unity gain amplifier 58 and a voltage-to-current converter 60. The latter device is utilized because the pen motor is essentially a current operated device. These components are shown schematically in FIG. 4 and in the control circuit of FIG. 7. Converter 60 incorporates a positioning adjustment 62 used during factory calibration to establish the basic recorder zero line. Unity gain amplifier 58 incorporates provision for additional factory calibration of pen deflection.

The main function control switch 64 is provided on the front of the instrument panel. The rotary operation of the switch 64 in combination with front and rear contact wafers 66, 68 illustrated in FIG. 5 controls the calibration and recording operation of the instrument. Switch positions 1 and 2 shown on the instrument panel in FIG. 1 correspond to the TIP and BASE contact positions of the switch illustrated in FIG. 5. With further reference to FIG. 5, when switch 64 is in the TIP, BASE or BOTH positions, power indicator light 70 should be lit. This indicator light is on the bottom, front face of the instrument panel as illustrated in FIG. 1. A 15 volt regulated power supply is provided to the instrument from a 115 volt power source by transformer 72. A second transformer 74 provides the low voltage required for pen heater 26.

Analog switch 56 is part of the multiplexer. The recording and monitoring instrument includes control means operative to condition switch 56 to receive input signals alternately from the two sensing devices 6 and 8, and their respective bridge circuits 32 and 34. Analog switch 56 transmits these input signals alternately from bridge circuits 32 and 34 to pen motor 22 through amplifier 58 and converter 60. In response to these signals, pen motor 22 actuates recording pen 20 so as to record two separate traces which reflect and separate diagnostic signals received from sensing devices 6 and 8.

FIGS. 4 and 7 illustrate the control means utilized to cycle analog switch 56 between the two input signals. The preferred control device is a clock oscillator 76. This clock oscillator emits control signals at predetermined time intervals which are inputted to analog switch 56 through a frequency divider 78 so as to cycle switch 56 between the two input signals at a desired frequency. As noted above, these input signals are independently transmitted to analog switch 56 from the output bridge circuits 32 and 34. As is indicated in FIGS. 5, 6 and 7, the output signals from second stage amplifiers 38 and 42 are transmitted from terminals points 80 and 84 to pin connectors 82 and 86 connected to input terminals 88 and 90 of analog switch 56. Referring now particularly to FIG. 7, when control terminal 92 of analog switch 56 is high, input terminal 88 is connected to switch output terminal 94. When control terminal 92 is low, input terminal 90 is connected to output terminal 94 of switch 56. Output terminal 94 drives pen motor 22 through intermediate amplifier 58 and converter 60 as noted above. To this end output terminals 96 and 98 are connected to pen motor 22 as illustrated in FIGS. 7 and 5.

The state of analog switch output terminal 94 is determined by frequency divider 78 connected between clock oscillator 76 and analog switch 56. The output of clock oscillator 76 is a square wave with a duty cycle of approximately 50 percent and a zero to plus 15 volt excursion. The 15 volt half of the clock cycle turns on transistor 100 which in turns toggles frequency divider 78. Frequency divider 78 is a toggle flip-flop; its output changes state on the negative going edge of the input pulse, hence the output frequency is half the input frequency. When the output at terminal 102 of frequency divider 78 is high, transistor 104 turns on and drives control terminal 92 of analog switch 56 low. Control terminal 92 remains low for a full oscillator clock cycle, then switches high for a full clock cycle, and so on. In this manner analog switch 56 is cyclically conditioned to alternately output signals from the two bridge circuits 32 and 34 received through connectors 82 and 86.

Since it is contemplated that the instrument of this invention will find particular application for monitoring and recording diagnostic signals over long time intervals on the order of eight hours or more, chart drive motor 24 advances recording paper 16 at the relatively slow speed of 20 centimeters per hour. This chart speed assures that an eight hour record has adequate resolution but is of manageable length. In order to avoid undesired marking and shading between the two recorded traces as illustrated in FIGS. 2 and 3 at such a relatively low chart speed, pen heater 26 is cycled off and on so as to be de-energized during switching excursions of recording pen 20 between the two traces. This is accomplished by signal relaying means connected between clock oscillator 76 and pen heater 26. As indicated in FIGS. 4 and 7, this signal relaying means preferably takes the form of a silicone controlled rectifier (SCR) 106. The output from SCR 106 is connected through terminal connectors 108 and 110 with pen heater 26 as indicated in FIGS. 5 and 7. Each pulse of clock oscillator 76 triggers SCR 106 so that pen heat turns off and on at the basic oscillator frequency. The 15 volt half of the clock cycle triggers SCR 106 and turns pen heat on during the 15 volt half of the clock cycle. However, since frequecy divider 78 operates as set forth above to trip analog switch 56 every other clock pulse to alternate the signal recording intervals between the two sensors at half the clcok oscillator frequency, pen heater 26 is turned off during the last half of each recording interval. Thus, switching of pen 20 between traces by analog switch 56 occurs when the pen has has maximum opportunity to cool down. This ensures that there is little or no pen marking between traces.

Clock oscillator 76 and frequency divider 78 operate to cycle analog switch 56 so as to switch between the two trace signals at a frequency of less than once every one-half second. The switching rate of pen 20 between traces by means of analog switch 56 is preferably as slow as once every second. This has proven to be a desirable frequency of pen switching between signal traces at the preferred, relatively slow chart speed of 20 centimeters per hour. Faster chart speeds may of course be used. However, for long recording intervals of eight hours or more, as are encountered in nocturnal penile tumescence monitoring, a chart speed of greater than 50 centimeters per hour would generate an excessive amount of chart paper for handling and study.

Because strain gauges 6 and 8 and the lead wire connections thereto are rather delicate and easily broken, warning circuits are provided to give visual indication if either of the strain gauges is broken or becomes disconnected. Preferably, the visual indicators are warning lights 112 and 114, these waring lights being positioned on the front panel of control cabinet 1 as shown in FIG. 1. With reference to FIGS. 4 and 6, it may be seen that the warning lights 112 and 114 are wired in separate warning circuits. The output of each of the second amplifier stages 38 and 42 for the bridge circuits of the two strain gauges goes to separate comparator controllers 116 and 118 for the warning lights as well as to analog switch 56 through connection terminals 80 and 84. Current to analog switch 56 as well as to the comparators 116 and 118 is limited by resistors 120 and 122. Voltage dividers 124, 126 and 128, 130 establish the set points of the two comparators 116 and 118, respectively. The output from these comparators is under the control of a clock oscillator 138. When the voltage input to either comparator 116 or 118 from either one of the bridge circuit amplifiers 38 or 42 exceeds the set point the output terminal of the corresponding comparator goes high and turns on the associated transistor 132 or 134. When either transistor 132 or 134 conducts, it connects output terminal 136 of clock oscillator 138 to connector terminal 140 or 142. As FIG. 5 indicates, connector 142 goes to plus 15 volts through warning light 114 when function switch 64 on the front panel of the instrument is in BASE or BOTH position. Connector 140 goes to chassis ground by way of warning light 112 when the selector or function switch 64 is in TIP or BOTH position. The two warning lights comprise light emitting diodes (LED) as indicated in FIG. 5. Thus, when connected into the circuit, warning light 112 will turn on during the high half of the clock cycle and warning light 114, when connected into the circuit, will turn on during the low or ground half of the clock cycle. Any type of mualfunction of either one of the strain gauges 6 or 8 resulting in a disruption of normal output voltage to comparators 116 or 118 will cause the respective warning light 112 or 114 to start blinking.

Prior to utilization of the monitoring and recording instrument to detect and record changes in the size of any anatomical member, the two strain gauges must be calibrated. This is necessary to ensure that the two trace signals are recorded on the appropriate zero line at a desired displacement from each other. For this purpose a calibration dummy of cylindrical shape having small and large diameter ends is utilized. With the cable assemblies 10 and 12 from the two strain gauges connected to the instrument through plug in terminals 2 and 4, and power cord 28 plugged into a 115 volt receptacle, calibration is carried out utilizing function switch 64 and calibration adjustments 44, 46, 48 and 50. For purposes of nocturnal penile tumescence monitoring, one of the strain gauges is designated the TIP gauge and the other is designated the BASE gauge corresponding to the locations of the two strain gauges on the subject's penis. The settings for function switch 6 have been designated TIP and BASE in FIG. 5 corresponding to switch positions 1 and 2 in FIG. 1 for purposes of reference with respect to the application of the instrument to nocturnal penile tumescence (NPT) monitoring. With function switch 64 turned to the BASE or setting 2 position, the BASE gain adjustment knob 50 is set at approximately the center of its travel position with the pointer at 12 o'clock. The loop of the BASE gauge 8 is placed on the small diameter end of the calibration dummy and the BASE zero line knob 46 is adjusted for a pen deflection of predetermined value, such as, 10 millimeters. The loop of the same BASE gauge 8 is then placed on the large diameter end of the calibration dummy and the BASE gain adjustment knob 50 is adjusted for a pen deflection of a greater magnitude, such as, 25 millimeters. The function switch 64 is then turned to the TIP or setting 1 position and the other or TIP gauge 6 is calibrated in the same manner. However, the zero line and gain adjustment knobs 44 and 48 for the other strain gauge are adjusted so as to provide the predetermined displacement between the two traces. This is accomplished by adjusting the zero line and amplitude gain knobs 44 and 48 to provide a predetermined, increased increment of pan deflection on the order of 10 millimeters, greater than the corresponding setting utilized for the BASE gauge 8.

After the instrument has been calibrated in the foregoing manner an NPT monitoring operation is undertaken by turning function switch 64 to the BOTH position to record both signal traces. The calibrated strain gauges 6 and 8 are then positioned around the penis of the subject as illustrated in FIG. 1. First, strain gauge 8 is positioned around the base of the penile shaft, then strain gauge 6 is positioned around the tip of the penis directly behind the glans. With function switch 64 in the BOTH position, monitoring is undertaken for a predetermined period of time. Input from both strain gauges will be recorded in the manner indicated in FIGS. 2 and 3. The TIP trace signals are recorded as trace 6a, and the BASE signals are recorded as trace 8a corresponding to strain gauges 6 and 8, respectively. The NPT monitor measures minute variations in penile size during the Rapid Eye Movement stages of sleep. The cycling operation of analog switch 56 as described above sends alternate drive signals from the two strain gauge sensors 6 and 8 to pen motor 22 causing it to move pen 20 so as to record two separate traces indicative of variations in penile tumescence at the tip and base of the penis. Measuring penile tumescence at both the base and tip has proven to be particularly effective in detecting all etiologies of impotence. Test results form the NPT monitor utilized in this manner help the physician to gain a clear and more object view of the part that organic causes play in male erectile impotence and to better determine the appropriate course of psychological or medical therapy. The signal tracings in FIG. 2 indicate significant tumescence activity. Organic impotence can be ruled out in this case. The tracings shown in FIG. 3 indicate no tumescence activity thereby strongly suggesting that impotence is of an organic nature.

Sensing devices of various kinds other than strain gauges 6 and 8 could be used to sense and generate signals to the instrument. For the particular applications of measuring changes in the size of anatomical members, ring type strain gauges of the construction disclosed herein have proven to be particularly effective. In addition to NPT monitoring, such strain gauges may be used to monitor changes in size of any member. It is contemplated that various changes may be made in the size, shape and construction of the various components and circuits of the recording instrument disclosed herein without departing from the spirit and scope of the invention as defined by the following claims.

What is claimed is:

1. Apparatus for simultaneously monitoring electrical signals from two, separate sensing devices and recording same on a single, multiplexing strip chart recorder, comprising:
   a strip chart recorder comprising:
      a movable pen disposed in trace producing relation to heat sensitive recording paper;
      a motor drivingly connected to said pen;
      a heater on said pen;
      drive means for advancing said recording paper past said pen at a predetermined speed;
   electrical circuit means connecting said pen motor and said pen heater to a power source and comprising:
      switch means interconnected to said pen motor for transmitting drive signals thereto;
      two separate sensing devices connected to said switch means, said sensing devices being selectively positionable at different monitoring locations to detect changes in a condition to be monitored and trigger the generation of signals in response to same;
      control means connected to said switch means and operative to emit control signals at predetermined time intervals to condition said switch means to receive input signals alternately from said two sensing devices at predetermined time intervals, and said switch means transmitting said input signals alternately from said two sensing devices to said pen motor, whereby said motor actuates said pen so as to record two separate traces on said recording paper corresponding to respective ones of said input signals from said two sensing devices; and
      signal relaying means connected between said control means and said pen heater and operative to selectively transmit an energizing signal to said pen heater in response to control signals from said control means in synchronization with the alternate conditioning of said switch means, at such frequency that said pen heater is de-energized during switching excursions of said pen between said two traces.

2. Apparatus as defined in claim 1 wherein:
   said control means comprises a clock oscillator emitting pulse signals at a predetermined frequency.

3. Apparatus as defined in claim 2 wherein:
   said control means further comprises a frequency divider in said circuit means between said clock oscillator and said switch means, said frequency divider having an output frequency to said switch means which is one-half the frequency of input control signals from said clock oscillator, whereby said frequency divider trips said switch means to switch between input signals from said two switching devices on every other pulse signal from said clock oscillator; and
   said signal relaying means operates on basic clock oscillator frequency and transmits said pulse signals to said pen heater to cycle the pen heater on and off with every pulse signal from said clock oscillator, whereby said pen heater is de-energized and cools down during the last half of each recording interval and switching movement of said pen between traces occurs after the pen heater has cooled down, thereby substantially eliminating pen marking between traces.

4. Apparatus as defined in claim 2 wherein:
said clock oscillator emits said control pulse signals at a frequency of less than one pulse per one-half second.

5. Apparatus as defined in claim 1 wherein:
said drive means advances said recording paper at a speed less than fifty centimeters per hour.

6. Apparatus as defined in claim 1 wherein:
said sensing devices comprise elastomer strain gauge rings which change impedance as they expand and contract with variations in the circumference of an anatomical member around which they are positioned.

7. Apparatus as defined in claim 6 wherein:
each of said strain gauges comprises one leg of a separate bridge circuit; and
separate amplifier means connected in said circuit means to independently receive output signals from each of said strain gauges and transmit separate, amplified signals to said switch means.

8. Apparatus as defined in claim 7 wherein:
one of said amplifier means incorporates bias means effective to add a predetermined increment to the signal outputted by one of said bridge circuits to displace the trace of said signal from the trace of the other signal from the other bridge circuit.

9. Apparatus as defined in claim 6 wherein:
said electrical circuit means comprises warning signal means and means for actuating same in response to a magnitude of signal triggered by either one of said strain gauges in comparison with a normal signal range which indicates a malfunction of said first or second strain gauge.

10. Apparatus for monitoring and recording nocturnal penile tumescence comprising:
a movable pen disposed in trace producing relation to heat sensitive recording paper;
a motor drivingly connected to said pen;
a heater on said pen;
drive means for advancing said recording paper past said pen at a predetermined speed;
electrical circuit means connecting said pen motor and said pen heater to a power source;
switch means interconnected to said pen motor in said electrical circuit means for transmitting drive signals thereto;
a first tumescence responsive strain gauge at one end of a subject's penis;
first electrical means interconnected between said first strain gauge and said switch means in said electrical circuit means and operative to generate a first signal responsive to changes in the impedance of said first strain gauge caused by variations in penile tumescence;
a second tumescence responsive strain gauge on the subject's penis at a longitudinally spaced location from said first strain gauge;
second electrical means interconnected between said second strain gauge and said switch means in said electrical circuit means and operative to generate a second signal responsive to changes in the impedance of said second strain gauge caused by variations in penile tumescence at said longitudinally spaced locations; and
control means connected to said switch means and operative to emit control signals at predetermined time intervals to condition said switch means to alternatively receive said first and second signals from said first and second strain gauges at predetermined time intervals, and said switch means transmitting said first and second signals alternately to said pen motor, whereby said pen motor drives said pen to record two separate traces on said recording paper indicating penile tumescence as sensed by said strain gauges.

11. Apparatus as defined in claim 10 wherein:
said first and second strain gauges are positioned at the base and tip of a subject's penis.

12. Apparatus as defined in claim 11 wherein said strain gauges are mercury filled, elastomer rings.

13. Apparatus as defined in claim 10 wherein:
said electrical circuit means comprises warning signal means and means for energizing same in response to a magnitude of said first or second signal in comparison with a normal signal range which indicates a malfunction of said first or second strain gauge.

14. Apparatus as defined in claim 13 wherein:
said warning signal means comprises first and second warning indicator devices connected in said electrical circuit and said energizing means comprises first and second energizing means connected to each of said warning indicator devices and to said control means, whereby control signals from said control means are conducted by said energizing means to energize said first or second warning indicator device.

15. Apparatus as defined in claim 10 wherein:
said electrical circuit means includes amplifier means in the circuit of said first electrical means operative to add a predetermined amplitude increment to said first signal which provides a positive, visual displacement between said two traces on said recording papers.

16. Apparatus as defined in claim 10 wherein:
said control means comprises a clock oscillator which regulates said switch means to cycle between said two signals at a rate slower than once per half second.

17. Apparatus as defined in claim 10 wherein:
signal relaying means is connected in said electrical circuit means between said control means and said pen heater and operates to selectively transmit energizing signals to said pen heater from said control means in synchronization with the cycling of said switch means between said first and second signals so as to de-energize said pen heater during switching excursions of said pen between said two traces, whereby undesired marking and shading between said traces will be avoided even at relatively slow chart speeds.

18. Apparatus as defined in claim 17 wherein:
said drive means advances said recording paper at a speed of less than fifty centimeters per hour.

19. Apparatus as defined in claim 17 wherein:
said signal relaying means comprises a silicone controlled rectifier.

* * * * *